(12) United States Patent
Lusso et al.

(10) Patent No.: US 8,012,719 B2
(45) Date of Patent: Sep. 6, 2011

(54) METHOD FOR THE QUANTITATIVE DETECTION OF NUCLEIC ACIDS

(76) Inventors: Paolo Lusso, Milan (IT); Mauro Malnati, Milan (IT); Giulia Cassina, Muggio' (IT)

( * ) Notice: Subject to any disclaimer, the term of this patent is extended or adjusted under 35 U.S.C. 154(b) by 0 days.

(21) Appl. No.: 12/133,561

(22) Filed: Jun. 5, 2008

(65) Prior Publication Data

US 2009/0029373 A1    Jan. 29, 2009

Related U.S. Application Data

(60) Continuation-in-part of application No. 11/169,694, filed on Jun. 30, 2005, now Pat. No. 7,384,769, which is a division of application No. 09/831,820, filed as application No. PCT/EP99/08847 on Nov. 17, 1999, now Pat. No. 7,029,843.

(30) Foreign Application Priority Data

Nov. 17, 1998 (IT) .................................. MI98A2491

(51) Int. Cl.
*C12P 19/34* (2006.01)
(52) U.S. Cl. ..................................... 435/91.2; 435/91.1
(58) Field of Classification Search .................. 435/91.2
See application file for complete search history.

(56) References Cited

U.S. PATENT DOCUMENTS

| 6,395,470 B2 | 5/2002 | Walkerpeach et al. |
| 7,029,843 B1 | 4/2006 | Locatelli et al. |
| 7,384,769 B2 | 6/2008 | Locatelli et al. |
| 2005/0239128 A1 | 10/2005 | Locatelli et al. |

FOREIGN PATENT DOCUMENTS

| EP | 0 623 682 | 11/1994 |
| WO | WO 95/34684 | 12/1995 |

OTHER PUBLICATIONS

Gibson et al., Genome Research, vol. 6, pp. 995-1001, 1996.*
Gibson U. E. M. et al.: "A Novel Method for Real Time Quantitative RT-PCR" Genome Research, US, Cold Spring Harbor Laboratory Press, vol. 6, No. 10, Oct. 1996, pp. 995-1001.
Woudenberg T. M. et al.: "Quantitative PCR by Real Time Detection" Proceedings of the SPIE, vol. 2680, Jan. 1996.
Secchiero P. et al.: "Quantitative PCR for Human Herpesviruses 6 and 7" Journal of Clinical Microbiology, US, Washington, DC, vol. 33, No. 8, Aug. 1995, pp. 2124-2130.
Kennedy M. M. et al.: "Identification of HHV8 in Early Kaposi's Sarcoma: Implications for Kaposi's Sarcoma Pathogenesis" Molecular Pathology, vol. 51, No. 1, Feb. 1998, pp. 14-20.
Zimmermann K. et al.: "Technical Aspects of Quantitative Competitive PCR" Biotechniques, US, Eaton Publishing, Natick, vol. 21, No. 2, Aug. 1996, pp. 268-270, 272, 27.
Kennedy et al., "HHV8 and female kaposi's sarcoma", J. Pathol. (1997) 183:447-452.
Bai et al, "Quantitative polymerase chain reaction for human herpesvirus diagnosis and measurement of Epstein-Barr v irus burden in posttransplant lymphoproliferative disorder", Clinical Chemistry 43:10, pp. 1843-1849 (1997).

* cited by examiner

*Primary Examiner* — Gary Benzion
*Assistant Examiner* — Cynthia Wilder
(74) *Attorney, Agent, or Firm* — Nixon & Vanderhye P.C.

(57) ABSTRACT

Provided herein is a method for the quantitative detection of HHV-6 subtypes A and/or B based on the use of a calibrator, suitable primers and probes, and a nucleic acid polymerase with 5'-3' nuclease activity.

6 Claims, 5 Drawing Sheets

Figure 1

```
         61                          110
HHV6B  TGGAGGTTCG AGCAGCGGAA CCAAGAAGG CGAAAGTTG CAAGGACTTT
HHV6A  TGGAGGTTCG A  GCAGCGGAACAAGAATG    AATATTA C........
HBD40  TGGAGGTTCG AGCAGCGGAA CCAAGAATG. ...AATATTA    C........
 CO1   TGG     GGGTTCG ACAGCGGAA CCAAGAATG. ...AATATTA C........

111                          160
HHV6B    GGAAGGGATA CCAGCATGAC GACGATTCGG AATTAACCA ACTGTCGGAT
HHV6A    .......... ....  ..GAT GATGAATCGG AATTAACCGG ATTGTCGGAT
HBD40    .......... ....  ..GAT GATGACTCGG AATTAACCGG ACTGTCGGAT
 CO1     .......... ....  ..GAT GATGATTCGG AATTAACCGG ACTGTCGGAT 161                          210
HHV6B  ACAGACAGCG ACAA CGATGT CCAAAACTGT CACGGAGTAA GAAACACCGG
HHV6A  ACAGACAGCG ACAA CGAAGT CCAATGCTGT CAAGAAGTAA CAAAGGTCGG
HBD40  ACAGACA  GCG ACAACGAAGT CCAATGCTGT CAAGAAGTAA AAAACATCGG
 CO1   ACAGACAGCG ACAAC  GAAGT C CAATGCTGT GACAAAGTAA CAAAGGTCGG 211          250
HHV6B    TTCCAAGACG TACTCCTCAGATTTTTTAA TCCTGACTAT
HHV6A    CCCCAAGACCTACTCCTCAGAAACTTTAA TCCTGAGTAT
HBD40    TCCCAAGACG TACTCCTCAG AAAATTAA TCCTGAGTAT
 CO1     TCCCAAGACG TACTCCTCAG AAAATTAA TCCTGATTAT
```

*Italic bold* : HHV-6B primers and probe localization

Bold: HHV-6A primers and probe localization

<u>Underlined:</u> mismatch between HHV -6A and -6B sequences

Highlighted: HHV-6A mismatches

SEQUENCE LISTING

<160> NUMBER OF SEQ ID NOS: 11

<210> SEQ ID NO 1
<211> LENGTH: 22
<212> TYPE: DNA
<213> ORGANISM: Unknown
<220> FEATURE:
<223> OTHER INFORMATION: synthetic oligonucleotide

<400> SEQUENCE: 1
ccggaaaccg aacattactg aa                                              22

<210> SEQ ID NO 2
<211> LENGTH: 21
<212> TYPE: DNA
<213> ORGANISM: Unknown
<220> FEATURE:
<223> OTHER INFORMATION: synthetic oligonucleotide

<400> SEQUENCE: 2
ttacgtgagg atgatcgagg c                                               21

<210> SEQ ID NO 3
<211> LENGTH: 23
<212> TYPE: DNA
<213> ORGANISM: Unknown
<220> FEATURE:
<223> OTHER INFORMATION: synthetic oligonucleotide

<400> SEQUENCE: 3
ttttctgagg agtacgtctt ggg                                             23

<210> SEQ ID NO 4
<211> LENGTH: 19
<212> TYPE: DNA
<213> ORGANISM: Unknown
<220> FEATURE:
<223> OTHER INFORMATION: synthetic oligonucleotide

<400> SEQUENCE: 4
gcagcggaac caagaatga                                                  19

<210> SEQ ID NO 5
<211> LENGTH: 22
<212> TYPE: DNA
<213> ORGANISM: Unknown
<220> FEATURE:
<223> OTHER INFORMATION: synthetic oligonucleotide

<400> SEQUENCE: 5
caaggacttt ggaagggata cc                                              22

<210> SEQ ID NO 6
<211> LENGTH: 21
<212> TYPE: DNA
<213> ORGANISM: Unknown
<220> FEATURE:
<223> OTHER INFORMATION: synthetic oligonucleotide

```
<400> SEQUENCE: 6
ccgtgacagt tttggacatc g                                              21

<210> SEQ ID NO 7
<211> LENGTH: 19
<212> TYPE: DNA
<213> ORGANISM: Unknown
<220> FEATURE:
<223> OTHER INFORMATION: synthetic oligonucleotide

<400> SEQUENCE: 7
acgccaacag acctagcga                                                 19

<210> SEQ ID NO 8
<211> LENGTH: 19
<212> TYPE: DNA
<213> ORGANISM: Unknown
<220> FEATURE:
<223> OTHER INFORMATION: synthetic oligonucleotide

<400> SEQUENCE: 8
cttgacagca ttggacttc                                                 19

<210> SEQ ID NO 9
<211> LENGTH: 19
<212> TYPE: DNA
<213> ORGANISM: Unknown
<220> FEATURE:
<223> OTHER INFORMATION: synthetic oligonucleotide

<400> SEQUENCE: 9
atgacgacga ttcggaatt                                                 19

<210> SEQ ID NO 10
<211> LENGTH: 17
<212> TYPE: DNA
<213> ORGANISM: Unknown
<220> FEATURE:
<223> OTHER INFORMATION: synthetic oligonucleotide

<400> SEQUENCE: 10
cgaaggcgtg acttgcg                                                   17

<210> SEQ ID NO 11
<211> LENGTH: 20
<212> TYPE: DNA
<213> ORGANISM: Unknown
<220> FEATURE:
<223> OTHER INFORMATION: synthetic oligonucleotide

<400> SEQUENCE: 11
gaatgtcggc aagcaatctc                                                20
```

METHOD FOR THE QUANTITATIVE DETECTION OF NUCLEIC ACIDS

This application is a continuation-in-part of application Ser. No. 11/169,694, filed Jun. 30, 2005 now U.S. Pat. No. 7,384,769, which is a divisional of application Ser. No. 09/831,820, filed Jun. 5, 2001 (issued as U.S. Pat. No. 7,029,843), which is a U.S. national phase of PCT/EP99/08847, filed Nov. 17, 1999, which claims benefit of Italian Application No. MI98A002491, filed Nov. 17, 1998, the entire contents of each of which is hereby incorporated by reference in this application.

The present invention relates to a method for quantitative detection of nucleic acids from a biological fluid sample. More specifically the invention provides a method for the quantitative detection of HHV-6 subtypes A and/or B based on the use of a calibrator, suitable primers and probes, and a nucleic acid polymerase with 5'-3' nuclease activity.

The method of the invention may be suitably applied to diagnosis of viral and any other pathogenic agents.

BACKGROUND ART

A commonly used strategy to detect the presence of pathogens, in biological fluids, is the detection of an antigen (direct method) or a respective antibody (indirect method). However, this strategy, performed with immunometric techniques such as ELISA, IFA or Western Blotting, is limited because of the scarce quantitation accuracy, precision and sensitivity, of the different antibody cross-reactivity and of the impossibility to obtain precocious diagnosis.

Another approach relies on the detection of nucleic acids specific for each kind of molecular target from any biological source, using the amplification by polymerase chain reaction (PCR). This technique, in its more sophisticated version i.e. the quantitative competitive PCR (qcPCR), makes it possible to reach a high sensitivity and a quite accurate quantitative measure, as well as to obtain a diagnosis a short time after contact between the patient and the pathogen. Nevertheless the precision and accuracy of this system is assured in a narrow quantitation range, thus forcing the operator to multiply the number of replies (typically 8) of the sample under investigation; furthermore a long time and additional costs for the amplified product detection steps are necessary.

The first systems that assessed PCR kinetics in real time were based on an intercalating substance such as ethidium bromide. This substance binds to the polymerizing double strand DNA proportionally, enhancing its fluorescence in response to UV excitation; the fluorescence emitted from the intercalated ethidium molecules was registered by a CCD camera in a thermal cycler equipped to irradiate the samples with UV rays and plotted against the amplification cycle number (Higuchi et al., Biotechnology 10:413-417). The main limitation of this technique is that the signal is generated also from the unspecific PCR products.

Subsequently the method known as TaqMan, described in U.S. Pat. No. 5,210,015 was introduced. This method is based on the real time detection of the fluorescence deriving from the degradation, directly dependent on the nascent PCR product, of a labeled probe specifically hybridizing to the segment to amplify, by means of the Taq polymerase enzyme. The PCR reaction mix contains a non-extendable oligonlucleotide probe, labeled with two fluorescent molecules, a reporter at the 5' end, and a quencher at the 3' end; the probe sequence must be complementary to a region of the DNA under investigation located between the two annealing sites of the oligonucleotide primers.

During the PCR amplification reaction, the Taq Polymerase enzyme specifically activated by the primers starts duplicating the DNA under investigation; when the enzyme contacts the probe annealed to the DNA, cuts it by its 5' nuclease activity, removing it and consequently separating the fluorescent molecules; the emission from the reporter fluorochrome becomes thus measurable and, each DNA molecule being accompanied by a reporter molecule release, the total fluorescence is at any time proportional to the amplified DNA amount. The Sequence Detection System 7700 ABI PRISM (produced and distributed by Perkin Elmer) can work both as a DNA amplifier and a collector of fluorescence signals from samples during the PCR reaction. These signals are then processed by a software capable of extrapolating the starting DNA amount in the analyzed samples by a standard curve built with the fluorescence signals from samples with known DNA content. It must be noted that such a system is endowed with two specificity levels: the specific annealing of the primers and the specific annealing of the probe.

SUMMARY OF THE INVENTION

The invention provides a method applicable to the nucleic acid quantification techniques based on the polymerase and 5' nuclease activity of nucleic acid polymerases for the specific detection and quantification of the two subtype variants A and B of the human herpesvirus 6 (HHV-6), with enhanced sensitivity, accuracy and precision and a reduced measure variability.

The method of the invention is based on the use of a calibrator during the steps of extraction of the sample, target nucleic acid amplification and subsequent detection with suitable probes able to differentially hybridize to the calibrator and the target sequences.

The method of the invention can be applied to the absolute quantification of HHV-6 DNA from different biological sources in body liquids such as liquor, urine, plasma, serum, synovial fluid, as well as in human tissues, blood or purified Peripheral blood Mononuclear cells.

DETAILED DESCRIPTION OF THE INVENTION

The invention provides a method for the accurate and selective quantitation of HHV-6, subtypes A and B. The method of the invention is based on the addition of a calibrator to the PCR mix, wherein said calibrator is a nucleic acid containing two regions annealing to the primers SEQ ID NOs:1 and 2, one region annealing to a probe SEQ ID NO:7 located inbetween and two spacers containing from 1 to 30 nucleotides located between the primer- and probe-annealing regions, respectively, wherein said spacers are mismatched with both HHV-6 A and B nucleic acid sequences.

The calibrator primers and probe sequences maintain a Tm comparable to the Tm utilized for amplifying the HHV-6 A and B fragments calculated by the specific software Primer Express PE (Applied Biosystem), as reported in table 1.

According to the invention, a known amount of the calibrator, which is preferably inserted in a suitable plasmid, is added to the sample before extracting the HHV-6 nucleic acid. Gene extraction may be performed following a standard lysis-purification protocol by phenol-chloroform. The calibrator plasmid is expanded and accurately quantified by the spectrophotometer so as to add an exact amount of it to the samples to be extracted. Upon DNA extraction, samples thus contain a certain number of HHV-6 genomes and calibrator plasmid copies, dependent on the total yield of such an extraction; the HHV-6 DNA quantitation is thus possible, assuming such a yield to be identical for both the molecular species.

In a second step the amplification reaction is carried out with specific primers and probes, which can be selected by the "Primer Express" software (Perkin Elmer). The probes carry a fluorescent reporter label and a quencher label at their 5' and 3' ends, respectively, whereby fluorescence is generated by means of the polymerase enzyme activity during amplification. Examples of fluorescent labels include TET (tetrachloro-6-carboxy-fluorescein), JOE (2,7-dimethoxy-4,5-dichloro-6-carboxyfluorescein), HEX (hexachloro-6-carboxy-fluorescein), preferably TAMRA (6-carboxy-tetramethyl-rhodamine) and FAM (6-carboxy-fluorescein). The nucleic acid polymerase is a thermostable polymerase with 5'-3' nuclease activity, preferably a DNA polymerase, and more preferably a DNA polymerase derived from the *Thermus* species.

The primers and probes are designed to amplify both type A and type B HHV-6 strains with the same efficiency, to obtain very high diagnostic sensitivity. According to a preferred embodiment, the primers and probes specific for HHV-6 type A are identified in SEQ ID NOs: 4 and 5 (primers forward and reverse, respectively) and SEQ ID NO: 6 (probe), whereas those specific for HHV-6 type B are identified in SEQ ID NO: 7 and 8 (primers forward and reverse, respectively) and SEQ ID NO: 9 (probe).

The reaction can be carried out in any Real-time PCR apparatus that can work both as a DNA amplifier and a collector of fluorescence signals emitted from the reporter markers released upon polymerase nuclease activity.

The reaction in the presence of the target nucleic acid specific probe permits the quantification of the copy number of the extracted target nucleic acid ($N_o$). The reaction in the presence of the calibrator permits the quantification of the calibrator copy number recovered upon extraction ($C_o$). The reaction in the presence of both permits calculation of the total number of target templates and calibrator (T).

It is thus possible to calculate the percentage of the calibrator recovery yield R:

$$R = C_o/C,$$

from which the calibration factor (cal)

$$\text{cal} = 1/R$$

and thus the actual number of nucleic acid units in the sample before extraction are obtained:

$$N = N_o \times \text{Cal}$$

The relation $$T = N_o + C_o$$

ensures that the amplification efficiency of the standard and calibrator DNA remain identical.

The absence of calibrator amplification makes it possible to detect any false negatives (technical errors or presence of inhibitors), which represent one of the most important drawbacks when using amplification methods in clinical diagnostics. The reaction conditions are the same as those commonly adopted in qcPCR reactions (Petrik j. et al., J. Virol. Methods, 64:147-159, 1997). The reaction conditions can be modified in order to compensate for the competition events, more exactly the primer concentration, the polymerase enzyme concentration, the annealing/extension time, or the concentration of cofactors such as $MgCl_2$ can be modified.

The target nucleic acid can be DNA or RNA, preferably DNA, while primers and probes are preferably deoxyribonucleotide sequences. When the nucleic acid is RNA a previous retro-transcription step is required in order to obtain the corresponding DNA.

The target DNA (HHV6) molecule and the calibrator were amplified with the same kinetics, as evidenced by the following equations:

y=37.804+-3.4402×LOG(x) R=1.000 for the standard template amplification, and y=38.543+-3.568×LOG(x) R=0.998 for the calibrator template amplification.

The two molecules added in the same tube were correctly co-amplified, using standard PCR reactions, for more than 7 order of magnitude with no necessity to compensate for competitive events.

In order to carry out the simultaneous detection and quantification of target DNA and calibrator in a single tube the calibrator were derivatized at the 5' end with VIC (Pe Biosystem), a fluorescent molecule having an emission spectrum different from the one used for the target DNA molecule detection.

To eliminate the interference generated by the partial overlapping of the emission spectra of the two dyes, the calibrator PCR conditions was modified by reducing the primers and probe concentrations (final concentration 50 nM for both). The reduction of the emission signal of VIC reporter was achieved without modification of the Ct (Cycle threshold) value, thus allowing a reproducible quantification of the calibrator itself.

The spectral interference was completely avoided by adding the calibrator in a fixed concentration one log higher than the maximal amount of standard used in the reference curve (i.e. 10,000,000 copies of calibrator for a standard curve in which the highest concentration of standard was 1,000,000 copies reaction).

A great advantage of the described method is represented by the possibility to immediately identify the quality of the extracted material. A further advantage is represented by the possibility of simultaneously measuring the calibrator and the target nucleic acid in the same reaction tube. The possibility of detecting total inhibitors of amplification reaction from the samples allows the elimination of false negatives often occurring with known techniques. Moreover, the calibration does not necessitate further standardization, which is conversely required, for example, by the TaqMan technique (see Chatelard P. et al., J. Virol. Methods, 71:137-146, 1998).

The present invention also provides a kit to perform the method herein disclosed, said kit including a suitable calibrator, a probe specific for the target nucleic acid, two or more primers and a nucleic acid polymerase, as above described.

DESCRIPTION OF THE FIGURES

FIG. 1. Alignment of U-95 sequences showing the selected Real-Time PCR amplicons for the HHV-6 A or B subtype specific amplification. Italic bold characters: HHV-6B primers and probe localization. Bold characters: HHV-6A primers and probe localization. Underlined characters: mismatch between HHV-6A and -6B sequences. Highlighted characters: HHV-6A mismatches.

HHV-6 A: y=−3.44 log(x)+38.87, $r^2$=0.9993. HHV-6 B: y=−3.44 log(x)+39.17, $r^2$=0.9994. Calibrator: y=−3.44 log(x)+39.42, $r^2$=0.9992.

Figure 2:
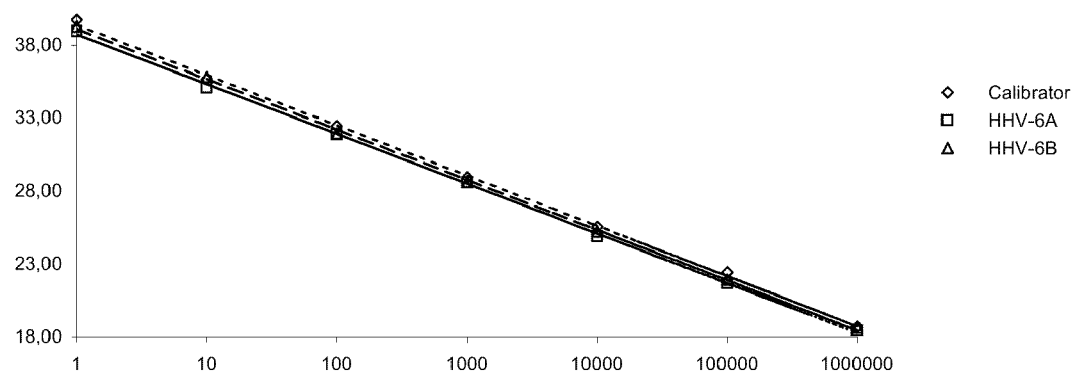
FIG. 2. Reference curves of the HHV-6 A and B subtype specific Real-Time TaqMan assays. Serial dilutions (from $10^0$ to $10^6$ HHV-6 genome equivalents) of the HHV-6 subtype A template (pVU6A; empty boxes), HHV-6 B template (pVU6B; empty triangles), and calibrator molecule (empty diamonds) run in triplicates. The equations resulting from the regression curves obtained by plotting the Ct values (y axis) against the indicated amount of DNA inputs (x axis) were.
Figure 3:
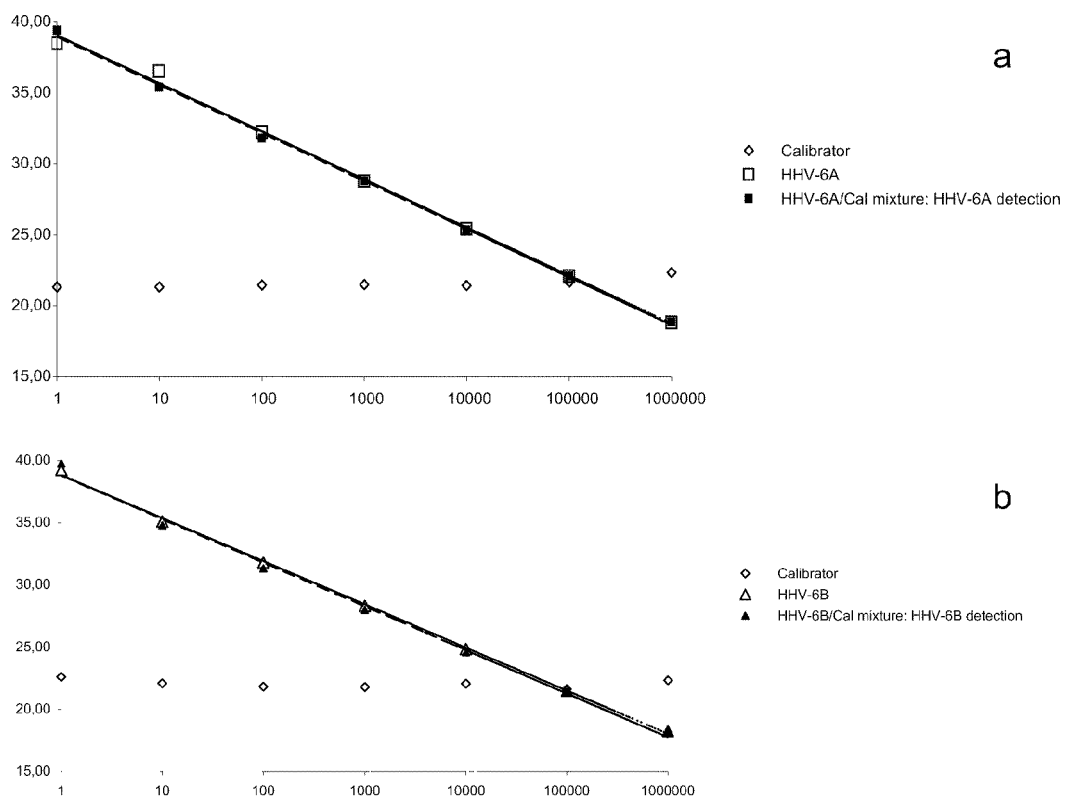

FIG. 3. Quantification of HHV-6A or B DNA is not affected by the presence of an excess of calibrator molecule. Quantification plots obtained amplifying either the pVU6A (FIG. 2A) or the pVU6B (FIG. 2B) reference constructs alone (FIG. 2A: empty box, solid line; FIG. 2B: empty triangle, solid line) or in the presence (FIG. 2A: filled box, dotted line; FIG. 2B: filled triangle, dotted line) of ≈200,000 copies/reaction of the calibrator molecule (FIG. 2A-B: empty diamonds).

Figure 4:
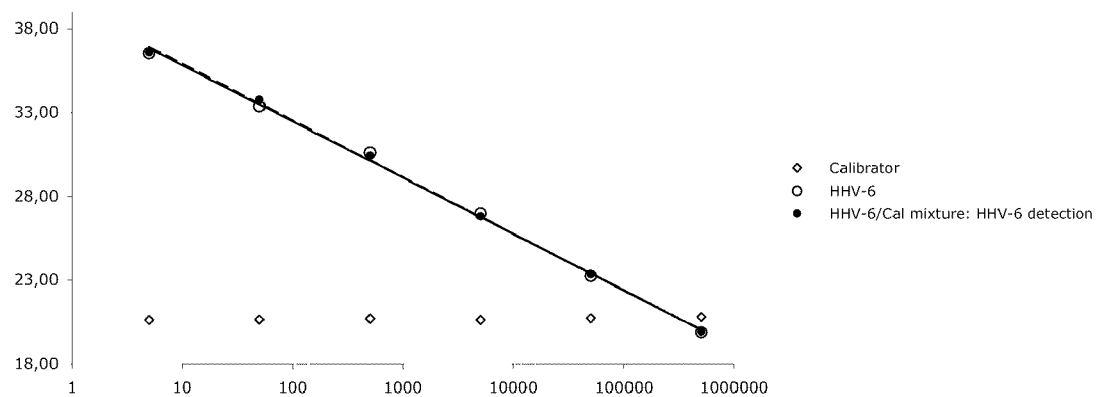

FIG. 4. Quantification of HHV-6 DNA is not affected by the presence of an excess of calibrator molecule. Quantification plots obtained amplifying the pVU46 plasmid containing the U-67 conserved region of HHV-6 in the absence (empty circle, solid line) or in the presence (filled circle, dotted line) of ≈200,000 copies/reaction of the calibrator molecule (empty diamonds).

Figure 5:
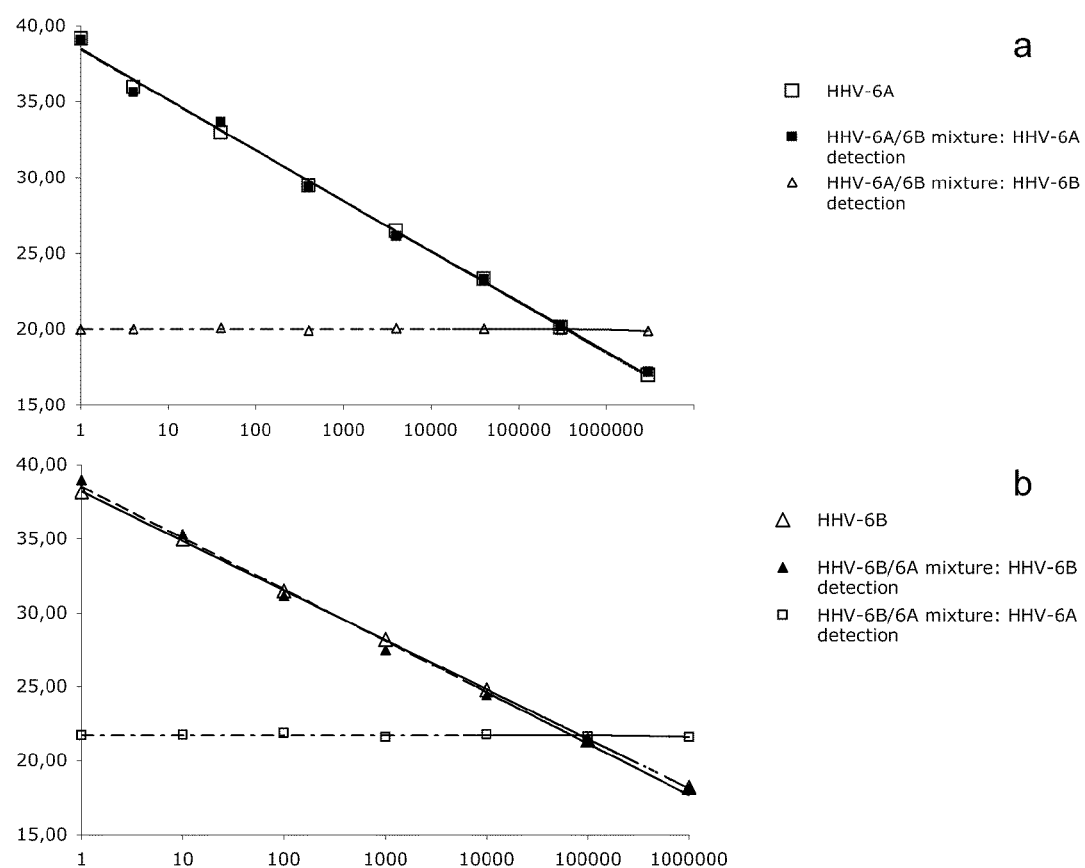

FIG. 5. Quantification of HHV-6A or B DNA is not affected by the presence of an excess of HHV-6 DNA belonging to both strains.

Quantification plots obtained amplifying either the pVU6A (FIG. 4A) or the pVU6B (FIG. 4B) reference constructs alone (FIG. 4A: empty box, solid line; FIG. 4B: empty triangle, solid line) or in the presence (FIG. 4A: filled box, dotted line; FIG. 4B: filled triangle, dotted line) of ≈500,000 (FIG. 4A: empty triangle) or ≈200,000 (FIG. 4B: empty box) copies/reaction of HHV-6B Z-29 and HHV-6A GS strains, respectively.

Experimental

Design of a PCR Real-Time System for HHV-6 Subtype Discrimination

In order to realize an efficient and subtype specific real-time PCR system for the accurate and selective quantification of both HHV-6 subtypes, we selected a region of the HHV-6 encoded U-95 open reading frame (ORF) corresponding to nt 145,001-145,251 for HHV-6 A (U1102 strain, gene bank accession no X83413) and to nt 146,943-147,223 for HHV-6 B (Z29 strain; gene bank accession no AF157706). The two fragments were amplified using the forward primer TAQ6F 5'-CGAAGGCGTGACTTGCG-3' (SEQ ID NO:10) and the reverse primer TAQ6R 5'-GAATGTCGGCAAGCAATCTC-3' (SEQ ID NO:11). PCR products were cloned into the pGEM T-Easy vector using the pGEM T-Easy Vector System cloning kit (Promega, Corp, Madison, Wis.) according to the manufacturer's instructions.

Both inserts were fully sequenced confirming 100% nucleotide identity with the reference sequences.

Given the limited numbers of HHV-6 A and B sequences available in data bases we cloned the selected region from 5 additional HHV-6 A isolates (strains GS, CO1, CO2, CO3 and DA) and 3 blood samples (HBD 40PL, CI 6980 and 6996) as well as from 1 HHV-6 β isolates (PL-1) and 4 blood samples derived from 2 healthy blood donors (HBD 33OF and EHBD 71), one patients affected by systemic sclerosis (SS 026PG), and one affected by Pitiriasis Rosea (PR 17MM). All the HHV-B derived sequences confirmed 100% identity with data base available sequences for the regions covering the HHV-6 B specific primers and probe whereas HHV-6 A sequences showed a certain degree of variability. In particular, the GS isolates was 100% identical to the U1102 sequence whereas all the CO isolates as well as the blood samples, although all maintained the two deletion fragments (26 and 4 nts) that are distinctive of the HHV-6 A strains, showed some additional nucleotides substitutions in the regions selected for the HHV-6 A specific primers and probe design (FIG. 1). In particular sequences derived from the three isolates CO1-3 showed three identical mismatches concentrated at the 5' end of the HHV-A specific probe and one mismatch in the 5' end of the reverse primer (FIG. 1 and table 1) whereas the sequences obtained from the blood samples showed mutations that did not affected neither primers nor the HHV-6 subtype A probe (FIG. 1).

Features of the HHV-6 A and B Specific Assays

To verify whether the selected PCR amplicons for distinguishing HHV-6 A and B subtypes possessed the requested features for an optimal PCR amplification, the PCR products were cloned into the pGEM T-Easy vector using the pGEM T-Easy Vector System cloning kit (Promega, Corp, Madison, Wis.) according to the manufacturer's instructions. The HHV-6 A and B inserts into the standard constructs (pVU6A and pVU6B) were first fully sequenced in order to verify the 100% identity with the reference sequences, then the plasmids were expanded, purified with the Qiagen plasmid Midi kit (Qiagen, Inc., Chatsworth, Calif.).

In order to generate the reference curve for HHV-6 A and B quantification, pVU6A and pVU6B plasmid DNA was measured by UV spectroscopy and three distinct sets of 10-fold dilutions were prepared, ranging from a DNA concentration of 0.405 µg/µl (equivalent to $10^{11}$ copies/µl) to a DNA concentration of $4 \times 10^{-4}$ fg/µl (equivalent to $10^{-1}$ copies per µl). The three series of samples were amplified by PCR in the same run of the 7700 ABI Prism sequence detector. The data generated a log-linear regression plot that showed a strong linear relationship ($r^2$>0.99) between the $\log_{10}$ of the starting copy number and the $C_t$ values (FIG. 2) for both HHV-6 A and B amnplicons. Moreover, as shown in FIG. 2, an optimal kinetics of the two reactions was obtained (HHV-6 A=−3.44 log(x)+38.8; HHV-6 B=−3.44 log(x)+39.1), ensuring either a high accuracy and reproducibility for both assays. In addition, a very wide dynamic range was observed (6 orders of magnitude), as the assays could discriminate template concentrations between 100 and 106 genome equivalents in a single PCR run.

In order to couple both assays with the same type of calibrator molecule, we modified the original calibrator sequence of the HHV-6 general assay avoiding disturbing secondary structures between the new sets of primers and probes but maintaining the TM described conditions for optimal primers and probe design (table 1). In order to obtain a higher Tm with shorter DNA sequences we designed all the new probe sequences with the addition of a 3' minor binding grove moiety (MGB). A calibrator sequence extensively mismatched with both HHV-6 A and B selected amplicons was then selected that shown a superimposable amplification kinetics and dynamic range with both assays (FIG. 2), thus ensuring an optimal control for PCR inhibitors and DNA recovery that did not interfere wither either HHV-6 A or B amplification (FIG. 3 A,B). The new type of calibrator molecule was additionally tested also with the general HHV-6 system showing no interference with the HHV-6 detection or quantification also when a single copy of HHV-6 standard was co-amplified in the presence of 250,000 copies of the calibrator molecule (FIG. 4).

Effects of Nucleotides Substitutions on HHV-6 Subtype A Quantifications and Specificity of HHV-6 Subtype Recognition by the Two Subtype A and B Real-Time PCR Assays In order to verify whether the nucleotide substitutions present in some HHV-6 A isolates (ie CO 1, 2 and 3) affected either the detection or DNA quantification, we synthesized both a reverse primer and probe homolog to the CO sequence and compared, in the same experiment, the quantification of the CO1 DNA obtained with the general HHV-6 real-time PCR with the ones measured with the HHV-6 A candidate system and its CO specific modification (table 2). As expected from the particular distribution of sequences mismatches, the quantification obtained with the candidate HHV-6 A system was superimponible to those obtained either with the HHV-6 A CO specific system or with the HHV-6 general assay (table 2).

To verify the specificity of both subtype restricted Real-Time assays we first measured the HHV-6 DNA load present in the supernatant of HHV-6 viral isolates cultures and in blood samples derived from HHV-6 infected individuals using the general HHV-6 system. Secondly, we reassessed the HHV-6 viral load using the two HHV-6 A and B specific assays. As shown in table 3, all the known viral isolates tested, with the exception of the DA isolate, as well as the clinical samples derived from several individuals were exclusively measured reciprocally only by one of the two systems, with an efficiency comparable to the one shown by the reference HHV-6 general system. The sole exception was represented by the DA isolates that has been shown to be formed mainly by a subtype A HHV-6 virus but containing also a minimal components of HHV-6 B. To further test the ability of the two assays in detecting and quantifying samples that contains DNA of both viral subtypes we prepare serial ten fold dilutions of the pVU6A and of the pVU6B reference plasmids in a fixed amount of the Z-29 strain (HHV-6 B subtype; 500,000 genome equivalent/reaction) or of the GS strain (HHV-6 A subtype; 200,000 genome equivalent/reaction) respectively. Neither the sensitivity (1 genome equivalent of HHV-6 A or B/reaction), nor the quantification of both reference constructs (FIG. 5 A-B), was affected by the presence of an excess of HHV-6 A or B strain respectively, as indicated by the similarity of the quantification plots (pVU6A alone: y=−3.241 log(x)+38.04; pVU6A plus Z29 DNA: 3.23 log (x)+38.02; pVU6B alone: y=−3.34 log(x)+38.22; pVU6B plus GS DNA: y=−3.34 log(x)+38.53). Therefore, since both assays are not affected by any means by the presence of large amounts of the opposite HHV-6 subtype, the combination of the two assays can determine the specific contribution of each HHV-6 subtype in dually infected individuals.

TABLE 2

Effects of nucleotide mismatches on HHV-6A quantification

| viral extract | general HHV-6 | HHV-6A | HHV-6A CO |
|---|---|---|---|
| CO1 | 22.58 ± 0.149 | 22.60 ± 0.064 | 22.61 ± 0.103 |
| CO2 | 22.13 ± 0.046 | 22.17 ± 0.064 | 22.16 ± 0.059 |
| CO3 | 22.35 ± 0.122 | 22.37 ± 0.020 | 22.40 ± 0.054 |

TABLE 3

Subtype specificity of HHV-6 A and B Real-Time PCR assays

| viral extract | general HHV-6 | HHV-6A | HHV-6B |
|---|---|---|---|
| GS | 21.14 ± 0.055 | 21.49 ± 0.032 | 40.00 ± 0.00 |
| U1102 | 25.86 ± 0.029 | 26.07 ± 0.012 | 40.00 ± 0.00 |
| CO1 | 22.58 ± 0.149 | 22.60 ± 0.064 | 40.00 ± 0.00 |
| CO2 | 22.13 ± 0.046 | 22.17 ± 0.064 | 40.00 ± 0.00 |
| CO3 | 22.35 ± 0.122 | 22.37 ± 0.020 | 40.00 ± 0.00 |
| HBD 40PL | 29.04 ± 0.273 | 29.21 ± 0.064 | 40.00 ± 0.00 |
| PL I | 21.84 ± 0.064 | 40.00 ± 0.00 | 21.74 ± 0.035 |
| Z29 | 23.46 ± 0.081 | 40.00 ± 0.00 | 22.47 ± 0.047 |
| HBD 33OF | 27.80 ± 0.176 | 40.00 ± 0.00 | 27.48 ± 0.006 |
| EHBD 71 | 26.71 ± 0.036 | 40.00 ± 0.00 | 26.77 ± 0.112 |
| SS 26PG | 22.56 ± 0.078 | 40.00 ± 0.00 | 22.17 ± 0.007 |
| PR 17MM | 21.19 ± 0.095 | 40.00 ± 0.00 | 21.12 ± 0.066 |
| DA | 23.13 ± 0.045 | 23.31 ± 0.031 | 37.01 ± 1.131 |

TABLE 1

Calibrator and HHV-6 A or B specific primers and probe sets

| System | | Sequence | Tm (° C.) |
|---|---|---|---|
| universal calibrator | Cal1 | 5'- CCGGAAACCGAACATTACTGAA -3' SEQ ID NO: 1 | 62, 4 |
| | Cal2 | 5'- TTACGTGAGGATGATCGAGGC -3' SEQ ID NO: 2 | 61, 6 |
| | Cal probe | 5'- ACGCCAACAGACCTAGCGA -3' SEQ ID NO: 7 | 71, 8 |
| HHV-6A | for | 5'- TTTTCTGAGGAGTACGTCTTGGG -3' SEQ ID NO: 3 | 61 |
| | rev | 5'- GCAGCGGAACCAAGAATGA -3' SEQ ID NO: 4 | 61, 4 |
| | probe | 5'- CTTGACAGCATTGGACTTC -3' SEQ ID NO: 8 | 72 |
| HHV-6B | for | 5'- CAAGGACTTTGGAAGGGATACC -3' SEQ ID NO: 5 | 60, 2 |
| | rev | 5'- CCGTGACAGTTTTGGACATCG -3' SEQ ID NO: 6 | 62 |
| | probe | 5'- ATGACGACGATTCGGAATT -3' SEQ ID NO: 9 | 72 |

The invention claimed is:

1. A method for the quantitative detection of a target nucleic acid from HHV-6 subtype variants A and/or B in a sample, which comprises the following steps:
   a) extraction of the nucleic acid from the sample with a calibrator previously added to the sample itself, wherein said calibrator is a nucleic acid containing two regions annealing to the primers SEQ ID NOS: 1 and 2, a third region annealing to the probe SEQ ID NO: 7 that is located in between said two regions and two spacers containing from 1 to 30 nucleotides located between the primer- and probe-annealing regions, respectively, wherein said spacers are mismatched with both HHV-6 A and B nucleic acid sequences;
   b) mixing the extracted target nucleic acid and calibrator with:
   i) the following primers pairs:
   a) SEQ ID NOs: 1 and 2 for the calibrator, and
   b) SEQ ID NOs: 3 and 4 for HHV-6 type A, and
   c) SEQ ID NOs: 5 and 6 for HHV-6 type B;
   ii) the following probes: SEQ ID NO:7 for the calibrator, SEQ ID NO:8 for HHV-6A and SEQ ID NO:9 for HHV-6B, wherein said probes carry a fluorescent reporter label able to generate a fluorescence signal and a quencher label at their 5' and 3' ends, respectively;

iii) a nucleic acid polymerase with 5'-3' nuclease activity;
c) performing a polymerization reaction whereby a signal associated with the reporters label is detected; and
d) quantification of the copy number of the extracted target nucleic acid and of the calibrator copy number recovered upon extraction.

2. The method according to claim 1, wherein said spacer within the calibrator contains from 5 to 10 nucleotides.

3. The method according to claim 1, wherein the probes have the 3' end blocked in order to prevent the extension by the polymerase.

4. The method according to claim 1, wherein the nucleic acid polymerase is thermostable DNA polymerase with 5'-3' nuclease activity.

5. The method according to claim 1, wherein said probes include a quencher label which reduces or avoids the reporter label fluorescence when the probes are free in solution.

6. Kit for the quantification of a HHV-6 subtype variants A and/or B nucleic acid from a sample, containing:

i) a calibrator that is a nucleic acid containing two regions annealing to the primers SEQ ID NOS: 1 and 2, a third region annealing to the probe SEQ ID NO: 7 that is located in between said two regions and two spacers containing from 1 to 30 nucleotides located between the primers- and probe-annealing regions, respectively, wherein said spacers are mismatched with both HHV-6 A and B nucleic acid sequences;
ii) the following primers pairs:
a) SEQ ID NOs: 1 and 2, and
b) SEQ ID NOs: 3 and 4, and
c) SEQ ID NOs: 5 and 6;
iii) the following probes: SEQ ID NO:7, SEQ ID NO:8 and SEQ ID NO:9 (HHV-6B), wherein said probes carry a fluorescent reporter label and a quencher label at their 5' and 3' ends, respectively;
iv) a nucleic acid polymerase with 5'-3' nuclease activity.

* * * * *